(12) United States Patent
Ruwwe et al.

(10) Patent No.: US 7,273,956 B2
(45) Date of Patent: Sep. 25, 2007

(54) PROCESS FOR PREPARING SOLUTIONS OF ALKALI METAL SALTS OF FUNCTIONALIZED ALCOHOLS

(75) Inventors: Johannes Ruwwe, Niederkassel (DE); Klaus Stadtmueller, Alzenau (DE)

(73) Assignee: Degussa AG, Duesseldorf (DE)

( * ) Notice: Subject to any disclaimer, the term of this patent is extended or adjusted under 35 U.S.C. 154(b) by 622 days.

(21) Appl. No.: 10/704,808

(22) Filed: Nov. 12, 2003

(65) Prior Publication Data

US 2004/0097759 A1 May 20, 2004

(30) Foreign Application Priority Data

Nov. 12, 2002 (DE) ............... 102 52 413

(51) Int. Cl.
*C07C 27/26* (2006.01)

(52) U.S. Cl. .................................... 568/921

(58) Field of Classification Search ................ 568/700, 568/921, 584, 590, 1
See application file for complete search history.

(56) References Cited

U.S. PATENT DOCUMENTS

| 4,235,902 | A | | 11/1980 | Durden, Jr. et al. |
| 4,372,974 | A | | 2/1983 | Fish et al. |
| 4,588,843 | A | | 5/1986 | Marlett |
| 5,034,248 | A | * | 7/1991 | Whitwell ................. 427/126.2 |
| 5,629,452 | A | | 5/1997 | Mosquet et al. |

FOREIGN PATENT DOCUMENTS

EP 0 518 013 12/1992
GB 1341375 12/1973
JP 63-061024 3/1988

OTHER PUBLICATIONS

U.S. Appl. No. 10/457,570, filed Jun. 10, 2003, Koehler et al.
U.S. Appl. No. 10/805,257, filed Mar. 22, 2004, Ruwwe et al.
U.S. Appl. No. 10/704,808, filed Nov. 12, 2003, Ruwwe et al.

* cited by examiner

*Primary Examiner*—Johann R Richter
*Assistant Examiner*—Lalitha Nagubandi
(74) *Attorney, Agent, or Firm*—Oblon, Spivak, McClelland, Maier & Neustadt, P.C.

(57) ABSTRACT

Alkali metal salt of formula (I): $MOYXR^1$ (I), and its solution can be prepared in high yields, particularly high space-time yields, and with high purities by reacting an alcohol of the formula (Ia): $HOYXR^1$ (Ia), in a solvent mixture with an alkali metal salt of formula (II): $MOR^2$ (II), or by reacting the alcohol (Ia) in a solvent mixture with an alkali metal hydroxide. Part of the liberated alcohol of formula (IIa): $HOR^2$ (IIa) or a part of the liberated water is distilled from the solvent mixture, initially, without addition of an entrainer. Subsequently, a remainder of the liberated alcohol of formula (IIa) or the liberated water is distilled from the solvent mixture with the aid of at least one organic solvent as entrainer. In formula (I) and in formula (II), M is Li, Na, K, Rb or Cs. In formula (I) and in formula (Ia): Y is $(C_1-C_8)$-alkylene, X is O, S or $NR^1$, and $R^1$ is H, $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl or $((C_1-C_8)$-alkyl$)_{1-3}$-$(C_3-C_{18})$-heteoraryl. In formula (II) and in formula (IIa), $R^2$ is methyl, ethyl, propyl, isopropyl, sec-butyl, isobutyl or tert-butyl.

13 Claims, No Drawings

PROCESS FOR PREPARING SOLUTIONS OF ALKALI METAL SALTS OF FUNCTIONALIZED ALCOHOLS

BACKGROUND OF THE INVENTION

1. Field of the Invention

The present invention relates to a process for preparing a solution of an alkali metal salt of a functionalized alcohol.

2. Discussion of the Background

Alkali metal salts of functionalized alcohols are employed in various fields, for example in the production of copper-containing films in the case of which the sodium salt of 2-amino-1-ethanol or the sodium salt of 2-methylamino-1-ethanol is used, as described in U.S. Pat. No. 5,034,248. Such alkali metal salts of functionalized alcohols can likewise be used for producing pharmaceutical products, for example, the sodium salts of 2-ethylamino-1-ethanol and of 2-amino-1-butanol, which are described in U.S. Pat. No. 4,235,902, or the sodium salt of 2-amino-1-ethanol, which is described in U.S. Pat. No. 4,372,974. A further application of the sodium salt of 2-amino-1-ethanol is described in JP 063 061 024, where it is used for preparing polyphosphazenes.

Alkali metal salts of functionalized alcohols can be prepared, for example, by reacting the free alcohols with alkali metals, as described, for example, in U.S. Pat. No. 4,235,902 or in U.S. Pat. No. 4,372,974. The reaction of functionalized alcohols with alkali metals can likewise be carried out in liquid ammonia as solvent. The disadvantage of these processes is the use of the very reactive metallic sodium for whose use costly safety precautions have to be taken.

A further possible way of preparing such alkali metal salts is the reaction of free alcohols with alkali metal hydrides. Such a reaction for preparing the sodium salt of 2-amino-1-ethanol is described in GB 1 341 375, where this salt is used for preparing heterocycles. A disadvantage of this process is that the expensive sodium hydride has to be used.

A further possibility is to react functionalized alcohols with alkali metal amides or organometallic compounds of alkali metals in order to obtain the alkali metal salts of the functionalized alcohols. Such reactions are described in U.S. Pat. No. 5,629,452, in which diphenylmethylpotassium, diphenylmethylsodium or sodium amide is used. These compounds are complicated to prepare or are expensive. Furthermore, at least in the case of diphenylmethylpotassium and diphenylmethylsodium, the diphenylmethane formed remains in the resulting reaction mixture after the reaction if no further work-up step is carried out.

EP 0 518 013 describes a process for preparing 1-alkoxy-2-dialkylaminoethanes. In the first step, the corresponding amino alcohols are converted by reaction with alkali metal salts of lower alcohols into the respective alkali metal salts of the functionalized alcohols. The reaction is completed by removing the lower alcohol formed from the reaction mixture, with an entrainer being added to the mixture before the work-up by distillation in order to remove the lower alcohol. However, an alternative also proposed by EP 0 518 013 is to employ the respective end products of the ether synthesis as entrainers. However, if the alkali metal salts of the functionalized alcohols are envisaged for purposes other than ether formation, this procedure is ruled out.

SUMMARY OF THE INVENTION

It is therefore an object of the present invention to provide a process for preparing alkali metal salts of functionalized alcohols, which, particularly on an industrial scale, is advantageous from economic and ecological points of view and is also superior to the processes of the prior art in terms of the space-time yield.

This and other objects have been achieved by the present invention the first embodiment of which includes a process for preparing a solution of an alkali metal salt of formula (I), comprising:

reacting an alcohol of the formula (Ia)

$$HOYXR^1 \qquad (Ia)$$

in a solvent mixture with an alkali metal salt represented by formula (II)

$$MOR^2 \qquad (II),$$

or reacting the alcohol of the formula (Ia) in a solvent mixture with an alkali metal hydroxide, thereby liberating an alcohol of formula (IIa) into the solvent mixture $$HOR^2 \qquad (IIa)$$

or liberating water into the solvent mixture; and distilling a part of the liberated alcohol of formula (IIa) or a part of the liberated water from the solvent mixture, initially, without addition of an entrainer; and subsequently, distilling a remainder of the liberated alcohol of formula (IIa) or the liberated water from the solvent mixture with the aid of at least one organic solvent as entrainer;

thereby obtaining said solution of said alkali metal salt of the formula (I)

$$MOYXR^1 \qquad (I);$$

wherein in formula (I) and in formula (II), M is Li, Na, K, Rb or Cs;

wherein in formula (I) and in formula (Ia):

Y is $(C_1-C_8)$-alkylene,

X is O, S or $NR^1$, and $R^1$ is H, $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl or $((C_1-C_8)$-alkyl$)_{1-3}$-$(C_3-C_{18})$-heteroaryl; and wherein in formula (II) and in formula (IIa), $R^2$ is methyl, ethyl, propyl, isopropyl, sec-butyl, isobutyl or tert-butyl.

In addition, the present invention relates to the product obtained by the above process and to a method of using the product for ether synthesis.

DETAILED DESCRIPTION OF THE INVENTION

The present invention relates to a process for preparing solutions of alkali metal salts of the formula (I)

$$MOYXR^1 \qquad (I)$$

wherein

M is Li, Na, K, Rb or Cs,

Y is $(C_1-C_8)$-alkylene,

X is O, S, $NR^1$, $R^1$ is H, $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-

$(C_3-C_8)$-cycloalkyl, $((C_1-C_8)$-alkyl$)_{1-3}$-$(C_6-C_{18})$-aryl, $((C_1-C_8)$-alkyl$)_{1-3}$-$(C_3-C_{18})$-heteroaryl, in a solvent mixture comprising the alcohol (Ia) corresponding to the formula (I), carrying out the reaction of the alcohol (Ia) corresponding to the formula (I) with the alkali metal salt of the formula (II) which is based on the corresponding alcohol (IIa)

$$MOR^2 \qquad (II)$$

wherein

M is as defined above, and $R^2$ is methyl, ethyl, propyl, isopropyl, sec-butyl, isobutyl or tert-butyl, or carrying out the reaction of the alcohol corresponding to the formula (I) with the alkali metal hydroxide. Part of the liberated alcohol (IIa) or the liberated water is firstly distilled from the solution without addition of an entrainer. The remainder is subsequently distilled from the solution with the aid of at least one further organic solvent as entrainer. This process, quite surprisingly, but no less advantageously, achieves the stated object. It was not to be foreseen that the liberated lower alcohol or the water can be distilled from the reaction mixture without addition of an entrainer, down to a particular proportion, without secondary reactions which would reduce the yield and product purity occurring in the relatively concentrated mixture. In addition, the smaller amount of distillate results in a reduction in the distillation time, which firstly helps to increase the space-time yield and secondly reduces the thermal stress on the products during the distillation.

Preferred compounds of the formula (I) are alkali metal salts of alcohols (Ia). In such alkali metal salts, M is Li, Na, K, Rb or Cs; Y is $(C_1-C_8)$-alkylene; X is $NR^1$; $R^1$ is H or $(C_1-C_8)$-alkyl.

Very particular preference is given to alkali metal salts of alcohols selected from the group consisting of aliphatic amino alcohols, e.g. 2-aminoethanol.

As alkoxide (II), all alkoxides which a person skilled in the art would consider for this purpose can be used in the above-described process. The inexpensive alkali metal salt of methanol or ethanol is preferably employed for deprotonation. The alkoxides can be used as solutions or in the solid state. The salts are preferably employed in the solid state so as to keep the distillate stream as small as possible and to avoid further mixing of different solvents. The alkoxide (II) is based on alcohols (IIa).

In principle, a person skilled in the art can make a free choice of entrainer as long as it is suitable for the desired purpose, i.e. it should have a boiling point which is greater than that of the liberated alcohol (IIa) $R^2OH$ or $H_2O$ or can remove a large amount of the alcohol or water to be separated off from the reaction mixture by azeotrope formation. Furthermore, it is preferred to use an entrainer which is inert so that residues of this entrainer can remain in the reaction mixture without causing concerns that a subsequent reaction of alkali metal salts of the functionalized alcohols will be adversely affected.

An organic solvent is used as an entrainer. The organic solvent is selected from the group consisting of linear and cyclic aliphatic hydrocarbons, aromatic hydrocarbons, compounds of the formula (III)

$$R^1(XY)_n XR^1 \qquad (III)$$

wherein n=1 or 2, $R^1$, in each case independently of one another, X, in each case independently of one another, and Y are as defined above, and alcohols of the formula (IV)

$$R^3OH \qquad (IV)$$

wherein $R^3$ is $(C_4-C_8)$-alkyl, $(C_2-C_8)$-alkenyl, $(C_2-C_8)$-alkynyl, or $(C_3-C_8)$-cycloalkyl.

Preference is given to using entrainers selected from the group consisting of toluene, xylene, benzene, hexane, heptane, cyclohexane, methylcyclohexane and relatively nonacidic alcohols, e.g. n-butanol or ethylene glycol, and ethylenediamine and diethylenetriamine. Mixtures of at least two solvents can be used.

The alcohol (IIa) formed or the water of reaction, with or without entrainer, is advantageously distilled from the reaction mixture at a pressure of from 10 mbar to 15 bar. The pressure of the distillation includes all values and subvalues therebetween, especially including 50, 100, 200, 300, 400, 500, 600, 700, 800, 900 mbar, 1 bar, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, and 14.5 bar.

However, the distillation is preferably carried out under subatmospheric pressure, very particularly preferably in the range from 100 to 500 mbar or below, depending on technical feasibility. The subatmospheric pressure includes all values and subvalues therebetween, especially including 50, 100, 150, 200, 250, 300, 350, 400, and 450 mbar.

An important aspect of the present process is the fact that the alcohols or water resulting from the reaction of the alkali metal alkoxide or the alkali metal hydroxide used for deprotonation are distilled off from the reaction mixture after the reaction, initially, without addition of an entrainer. Any extent of this first distillation is suitable. However, the economics of the process and the obtainable product purity, which should be very high, are preferably used as a guide. Preference is given to distilling off from 10-90% by volume of the liberated alcohol (IIa) or water without entrainer, before the appropriate entrainers are added to the reaction mixture for further distillation. The amount of distilled off alcohol (IIa) or water includes all values and subvalues therebetween, especially including 15, 20, 25, 30, 35, 40, 45, 50, 55, 60, 65, 70, 75, 80, and 85% by volume.

However, under the abovementioned premises, very substantial removal of the constituents to be distilled off (water, alcohol (IIa)) is particularly preferable in the first distillation step. Thus, preferably 40-90, more preferably 50-90 and most preferably 70-90% of the alcohol (IIa) or water are distilled off in the first distillation.

In general, the procedure employed according to the present invention is to add solid alkali metal alkoxide (II) or alkali metal hydroxide to a functionalized alcohol (Ia) and to begin to distill off the water formed or the alcohol formed (IIa) from the mixture under reduced pressure. After the initial distillation, the entrainer is added to the reaction mixture and the distillation is continued until the concentration of the water of reaction or the alcohol formed has been reduced to an acceptable level, preferably below 100 ppm. The yield of product and its purity are from >90% to 99.9% or more. The yield includes all values and subvalues therebetween, especially including 90.5, 91, 91.5, 92, 92.5, 93, 93.5, 94, 94.5, 95, 95.5, 96, 96.5, 97, 97.5, 98, 98.5, 99 and 99.5%. The purity of the product includes all values and subvalues therebetween, especially including 90.5, 91, 91.5, 92, 92.5, 93, 93.5, 94, 94.5, 95, 95.5, 96, 96.5, 97, 97.5, 98, 98.5, 99 and 99.5%.

The solution containing the compound according to claim 1 can be further distilled to obtain to alkali metal salt without any solvent.

The functionalized alkoxides (I) present in solution are preferably used in the form of a solution in subsequent reactions, e.g. ether formation with alkyl halides. Owing to the fact that purity and yield of compounds of the formula (I) are as good as this, downstream products such as the ethers in question can be obtained in high yields and correspondingly good purities. This, combined with a relatively high space-time yield, is particularly surprising to a person skilled in the art in view of the prior art.

For the purposes of the present invention, $(C_1-C_8)$-alkyl is methyl, ethyl, n-propyl, isopropyl, n-butyl, isobutyl, sec-butyl, tert-butyl, pentyl, hexyl, heptyl or octyl, including all structural isomers.

$(C_1-C_8)$-alkylene is a $(C_1-C_8)$-alkyl radical which is bound via two bonds to the molecule in question. These radicals can be monosubstituted or polysubstituted by $(C_1-C_8)$-alkoxy, $(C_1-C_8)$-haloalkyl, halogen, $NH_2$, $NH(C_1-C_8)$-alkyl, $N[(C_1-C_8)$-alkyl$]_2$ or S—$(C_1-C_8)$-alkyl.

$(C_2-C_8)$-alkenyl is a $(C_1-C_8)$-alkyl radical as described above, with the exception of methyl, which has at least one double bond.

$(C_2-C_8)$-alkynyl is a $(C_1-C_8)$-alkyl radical as described above, with the exception of methyl, which has at least one triple bond.

$(C_1-C_8)$-acyl is a $(C_1-C_8)$-alkyl radical bound to the molecule via a —C=O function.

$(C_3-C_8)$-cycloalkyl radicals are cyclopropyl, cyclobutyl, cyclopentyl, cyclohexyl and cycloheptyl radicals, etc. These can be substituted by one or more halogens and/or N—, O—, P—, S-containing radicals and/or have N—, O—, P—, S-containing radicals in the ring, e.g. 1-, 2-, 3-, 4-piperidyl, 1-, 2-, 3-pyrrolidinyl, 2-, 3-tetrahydrofuryl or 2-, 3-, 4-morpholinyl. These can be monosubstituted or polysubstituted by $(C_1-C_8)$-alkoxy, $(C_1-C_8)$-haloalkyl, halogen, $NH_2$, S—$(C_1-C_8)$-alkyl, $(C_1-C_8)$-acyl, $(C_1-C_8)$-alkyl.

A $(C_6-C_{18})$-aryl radical is an aromatic radical having from 6 to 18 carbon atoms. Such radicals include, in particular, phenyl, naphthyl, anthryl, phenanthryl and biphenyl radicals. These can be monosubstituted or polysubstituted by $(C_1-C_8)$-alkoxy, $(C_1-C_8)$-haloalkyl, halogen, $NH_2$, S—$(C_1-C_8)$-alkyl, $(C_1-C_8)$-acyl, $(C_1-C_8)$-alkyl.

A $(C_7-C_{19})$-aralkyl radical is a $(C_6-C_{18})$-aryl radical bound to the molecule via a $(C_1-C_8)$-alkyl radical.

$(C_1-C_8)$-alkoxy is a $(C_1-C_8)$-alkyl radical bound to the molecule under consideration via an oxygen atom.

$(C_1-C_8)$-haloalkyl is a $(C_1-C_8)$-alkyl radical substituted by one or more halogen atoms.

For the purposes of the invention, a $(C_3-C_{18})$-heteroaryl radical is a five-, six- or seven-membered aromatic ring system having from 3 to 18 carbon atoms and having heteroatoms such as nitrogen, oxygen or sulfur in the ring. Examples of such heteroaromatics are, in particular, 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. These can be monosubstituted or polysubstituted by $(C_1-C_8)$-alkoxy, $(C_1-C_8)$-haloalkyl, halogen, $NH_2$, S—$(C_1-C_8)$-alkyl, $(C_1-C_8)$-acyl or $(C_1-C_8)$-alkyl.

A $(C_4-C_{19})$-heteroaralkyl is a heteroaromatic system corresponding to the $(C_7-C_{19})$-aralkyl radical.

Possible halogens are fluorine, chlorine, bromine and iodine.

Having generally described this invention, a further understanding can be obtained by reference to certain specific examples which are provided herein for purposes of illustration only, and are not intended to be limiting unless otherwise specified.

EXAMPLES

Example 1

According to the Invention

The sodium salt of 2-amino-1-ethanol in a mixture of 2-amino-1-ethanol and n-butanol was required, and it was necessary for the methanol content to be very low.

350 g (5.73 mol) of 2-amino-1-ethanol were admixed with 92 g (1.70 mol) of solid sodium methoxide. At a pressure of 400 mbar, 46 g of methanol were distilled off, which corresponded to about 84% of the theoretical amount. 199 g of n-butanol were subsequently added and a further 115 g of distillate were taken off at a pressure of 150 mbar to a temperature at the bottom of 110° C. A methanol concentration of only 0.013% was found.

Example 2

According to the Invention

The sodium salt of 2-amino-1-butanol in a mixture of 2-amino-1-butanol and toluene was required, and it was necessary for the methanol content to be very low.

350 g (3.93 mol) of 2-amino-1-butanol were admixed with 92 g (1.70 mol) of solid sodium methoxide. At a pressure of 400 mbar, 47 g of methanol were distilled off, which corresponded to about 84% of the theoretical amount. 200 g of toluene were subsequently added and a further 120 g of distillate were taken off at a pressure of 150 mbar to a temperature at the bottom of 120° C. A methanol concentration of only 0.011% was found.

Example 3

According to the Invention

The sodium salt of 2-amino-1-butanol in a mixture of 2-amino-1-butanol and n-butanol was required, and it was necessary for the methanol content to be very low.

350 g (3.93 mol) of 2-amino-1-butanol were admixed with 92 g (1.70 mol) of solid sodium methoxide. At a pressure of 400 mbar, 47 g of methanol were distilled off, which corresponded to about 84% of the theoretical amount. 205 g of n-butanol were subsequently added and a further 120 g of distillate were taken off at a pressure of 150 mbar to a temperature at the bottom of 123° C. A methanol concentration of only 0.011% was found.

Example 4

According to the Invention

The sodium salt of 2-amino-1-butanol in a mixture of 2-amino-1-butanol and n-butanol was required, and it was necessary for the methanol content to be very low.

350 g (3.93 mol) of 2-amino-1-butanol were admixed with 305 g (1.70 mol) of sodium methoxide solution (30% strength in methanol). At a pressure of 150 mbar, 244 g of methanol were distilled off, which corresponded to about 90% of the theoretical amount. 195 g of n-butanol were subsequently added and a further 120 g of distillate were taken off at a pressure of 150 mbar to a temperature at the bottom of 114° C. A methanol concentration of only 0.010% was found.

Example 5

Comparative Example

The sodium salt of 2-amino-1-ethanol in a mixture of 2-amino-1-ethanol and toluene was required, and it was necessary for the methanol content to be very low.

350 g (5.73 mol) of 2-amino-1-ethanol were admixed with 92 g (1.70 mol) of solid sodium methoxide. In a column having 26 theoretical plates, 51 g of methanol were distilled off at a pressure of 400 mbar to a temperature at the bottom of 171° C., which corresponded to about 94% of the theoretical amount. Further heating of the bottoms results in significant discoloration.

93 g of toluene were subsequently added. The residual methanol content was 0.71%.

Example 6

Comparative Example

The sodium salt of 2-amino-1-butanol in a mixture of 2-amino-1-butanol and toluene was required, and it was necessary for the methanol content to be very low.

350 g (3.93 mol) of 2-amino-1-butanol were admixed with 92 g (1.70 mol) of solid sodium methoxide and 195 g of toluene. In a column having 5 theoretical plates, 171 g of distillate were distilled off at a pressure of 150 mbar. The distillation bottoms were obtained in the form of a homogeneous mixture which had a methanol content of 2.22%.

German patent application 10252413.0, filed Nov. 12, 2002, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing a solution of an alkali metal salt of formula (I), comprising:
    reacting an alcohol of the formula (Ia)

$$HOYXR^1 \qquad (Ia)$$

in a solvent mixture with an alkali metal salt represented by formula (II)

$$MOR^2 \qquad (II),$$

or reacting the alcohol of the formula (Ia) in a solvent mixture with an alkali metal hydroxide,
    thereby liberating an alcohol of formula (IIa) into the solvent mixture $$HOR^2 \qquad (IIa)$$

or liberating water into the solvent mixture; and
    distilling a part of the liberated alcohol of formula (IIa) or a part of the liberated water from the solvent mixture, initially, without addition of an entrainer; and
    subsequently, distilling a remainder of the liberated alcohol of formula (IIa) or the liberated water from the solvent mixture with the aid of at least one organic solvent as entrainer;
    thereby obtaining said solution of said alkali metal salt of the formula (I)

$$MOYXR^1 \qquad (I);$$

wherein in formula (I) and in formula (II), M is Li, Na, K, Rb or Cs;
    wherein in formula (I) and in formula (Ia):
    Y is $(C_1-C_8)$-alkylene,
    X is O, S or $NR^1$, and
    $R^1$ is H, $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl or $((C_1-C_8)$-alkyl$)_{1-3}$-$(C_3-C_{18})$-heteroaryl;
    and
    wherein in formula (II) and in formula (IIa), $R^2$ is methyl, ethyl, propyl, isopropyl, sec-butyl, isobutyl or tert-butyl.

2. The process as claimed in claim 1, wherein the organic solvent used as an entrainer is selected from the group consisting of linear aliphatic hydrocarbons, cyclic aliphatic hydrocarbons, aromatic hydrocarbons, compounds of the formula (III)

$$R^1(XY)_nXR^1 \qquad (III)$$

wherein
    n=1 or 2,
    $R^1$, in each case independently of one another, X, in each case independently of one another, and Y, in each case independently of one another, are as defined in claim 1, and alcohols of the formula (IV)

$$R^3OH \qquad (IV)$$

wherein
    $R^3$ is $(C_4-C_8)$-alkyl, $(C_2-C_8)$-alkenyl, $(C_2-C_8)$-alkynyl or $(C_3-C_8)$-cycloalkyl.

3. The process as claimed in claim 1, wherein the both distillations are carried out at pressures of from 10 mbar to 15 bar.

4. The process as claimed in claim 1, wherein 10-90% by volume of the liberated alcohol (IIa) or of the liberated water are distilled off without entrainer.

5. The process according to claim 1, wherein in the alkali metal salt of formula (I) M is Li, Na, K, Rb or Cs; Y is $(C_1-C_8)$-alkylene; X is $NR^1$; and $R^1$ is H or $(C_1-C_8)$-alkyl.

6. The process according to claim 1, wherein in said alkali metal salt of formula (I), M is Li, Na, K, Rb, or Cs;
    Y is $(C_1-C_6)$-alkylene;
    X is $NR^1$; and
    $R^1$ is H.

7. The process according to claim 1, wherein in said alkali metal salt of formula (I), M is Li, Na, K, Rb or Cs;
    Y is $C_2$ alkylene;
    X is $NR^1$; and
    $R^1$ is H.

8. The process according to claim 1, wherein said entrainer is selected from the group consisting of toluene, xylene, benzene, hexane, heptane, cyclohexane, methylcyclohexane and mixtures thereof.

9. The process according to claim 1, wherein said entrainer is selected from the group consisting of n-butanol, ethylene glycol, ethylenediamine, diethylenetriamine and mixtures thereof.

10. The process according to claim 1, wherein said distillations are carried out at a pressure of from 100 to 500 mbar.

11. The process according to claim 1, wherein said a concentration of said liberated water or said liberated alcohol is below 100 ppm after said distillation with said entrainer.

12. The process according to claim 1, wherein a yield of said process is from >90% to 99.9%.

13. The process according to claim 1, wherein a purity of said alkali metal salt is from >90% to 99.9%.

* * * * *